(12) United States Patent
Kanai

(10) Patent No.: US 7,410,463 B2
(45) Date of Patent: Aug. 12, 2008

(54) OPTICAL SYSTEM FOR STEREOSCOPIC RIGID ENDOSCOPE

(75) Inventor: Moriyasu Kanai, Saitama-ken (JP)

(73) Assignee: HOYA Corporation, Tokyo (JP)

( * ) Notice: Subject to any disclaimer, the term of this patent is extended or adjusted under 35 U.S.C. 154(b) by 813 days.

(21) Appl. No.: 11/034,833

(22) Filed: Jan. 14, 2005

(65) Prior Publication Data

US 2005/0159641 A1    Jul. 21, 2005

(30) Foreign Application Priority Data

Jan. 15, 2004    (JP) .............................. 2004-007556

(51) Int. Cl.
- *A61B 1/06* (2006.01)
- *A61B 1/00* (2006.01)
- *A61B 1/04* (2006.01)
- *H04N 13/00* (2006.01)
- *H04N 15/00* (2006.01)
- *H04N 9/47* (2006.01)
- *H04N 13/04* (2006.01)

(52) U.S. Cl. .................... 600/166; 600/111; 348/45; 348/58

(58) Field of Classification Search ................ 600/111, 600/166; 348/45, 47, 49, 54, 57, 58
See application file for complete search history.

(56) References Cited

U.S. PATENT DOCUMENTS

| | | | | |
|---|---|---|---|---|
| 4,846,154 A | * | 7/1989 | MacAnally et al. | 600/171 |
| 4,862,873 A | * | 9/1989 | Yajima et al. | 600/111 |
| 4,873,572 A | * | 10/1989 | Miyazaki et al. | 348/45 |
| 5,142,642 A | * | 8/1992 | Sudo | 348/47 |
| 5,603,687 A | * | 2/1997 | Hori et al. | 600/166 |
| 5,689,365 A | * | 11/1997 | Takahashi | 359/362 |
| 5,944,655 A | * | 8/1999 | Becker | 600/166 |
| 6,338,711 B1 | | 1/2002 | Sekiya et al. | |
| 6,361,491 B1 | * | 3/2002 | Hasegawa et al. | 600/175 |
| 6,976,956 B2 | * | 12/2005 | Takahashi et al. | 600/166 |
| 7,101,334 B2 | * | 9/2006 | Takahashi | 600/166 |
| 2002/0082476 A1 | * | 6/2002 | Takahashi et al. | 600/173 |
| 2003/0083551 A1 | * | 5/2003 | Takahashi | 600/166 |

FOREIGN PATENT DOCUMENTS

JP    5-341207    12/1993

OTHER PUBLICATIONS

English Language Abstract of JP5-341207.

* cited by examiner

*Primary Examiner*—John P. Leubecker
*Assistant Examiner*—Philip R Smith
(74) *Attorney, Agent, or Firm*—Greenblum & Bernstein, P.L.C.

(57) ABSTRACT

An optical system for stereoscopic rigid endoscope is provided with first and second objective optical systems arranged to have a predetermined clearance therebetween and an optical path combining system that polarizes light passed through the first and second objective optical systems in directions perpendicular to each other. The optical path combining system parallelly shifts the optical axes of the first and second objective optical systems so that they coincide with each other. The shifting directions of the optical axes form an angle less than 90 degrees. A relaying optical system is provided inside the insertion unit of the endoscope. An optical axis of the relaying optical system is coaxial with the combined optical axes. An optical image separating system separates the light passed through the relaying optical system into first and second components that passed through the first and second objective optical systems and polarized by the optical path combining system, respectively.

9 Claims, 5 Drawing Sheets

OPTICAL SYSTEM FOR STEREOSCOPIC RIGID ENDOSCOPE

BACKGROUND OF THE INVENTION

The present invention relates to an optical system incorporated in a stereoscopic rigid endoscope.

Conventionally, a rigid endoscope has been widely used to observe inside of human bodies, machines, debris and the like. Conventional rigid endoscope has been provided with a single optical system and observation is performed with one eye. With such a conventional rigid endoscope, only a two-dimensional view can be observed. In order to carry out various treatment inside the object precisely, a three-dimensional view of the object is desired. For this purpose, recently, a stereoscopic rigid endoscope has been developed and used. An example of such a stereoscopic rigid endoscope is disclosed in Japanese Patent Provisional Publication No. 05-341207.

The stereoscopic rigid endoscope system described as a first embodiment in the publication is provided with a pair of object optical systems each including a polarization plate and a pair of eyepiece optical systems which respectively include polarization plates. According to the first embodiment, light passed through the objective optical systems are reflected by a pair of mirrors, which are arranged at opposite positions with a half mirror therebetween. The light reflected by the pair of mirrors is directed to the half mirror, by which the optical paths are combined to a single path. Then, the light is introduced to a tip end surface of a relay optical system. The light passed through and emerges from the proximal side end surface of the relay lens is divided to proceed along two different optical paths and is introduced into the pair of eyepiece optical systems, respectively. With use of the polarization plates, the polarized directions of the objective optical system and eyepiece optical system for right eye are aligned with each other, and the polarized directions of the objective optical system and eyepiece optical system for left eye are aligned with each other. Further, the polarization directions of the optical systems for right eye and left eye are adjusted to be perpendicular to each other.

According to a second embodiment in the publication, the stereoscopic rigid endoscope is provided with a single relaying optical system fixed in an insertion unit of the endoscope. In the vicinity of the distal end of the relaying optical system, an objective lens and a circular polarization plate are provided. In the vicinity of the proximal end of the relaying optical system, a polarization direction selecting device is provided. According to the second embodiment, the polarization plate is configured such that the polarization directions of a semi-circular area and the other of the semi-circular area are perpendicular to each other. The polarization direction selecting device is configured to alternately transmit two polarization components of the light emerging from the relaying optical system.

According to a third embodiment of the above-described publication, a pair of objective optical systems, which do not have the polarization plates, are provided at a tip portion of the insertion unit of the endoscope, and a polarization selecting device is provided in the vicinity of the proximal end of a relaying optical system which is fixed inside the insertion unit. According to the third embodiment, distances from the tip end surface of the insertion unit to each of the objective optical systems are the same, and the optical axes thereof are parallel with each other. Further, the optical axis of one of the objective optical systems coincides with the optical axis of the relaying optical system. The optical axis of the other objective optical system is finally arranged to coincide with the relaying optical system after bent by a mirror and polarization beam splitter in order. Further, the polarization beam splitter is configured such that the polarization direction thereof when the light is transmitted and the polarization direction when the light is reflected is perpendicular to each other.

As described above, in the stereoscopic rigid endoscope according to any one of the three embodiments, a single relaying optical system is used for both right and left eyes. Therefore, differences in optical performance for right and left eyes are suppressed.

However, according to the first embodiment, since the pair of mirrors are arranged on opposite sides of the half mirror. Therefore, it is difficult to downsize the tip end radius of the insertion unit.

According to the second embodiment, the right and left images are obtained by dividing a pupil of a single objective lens. Therefore, a substantially half of the diameter of the incident pupil of the objective optical system is regarded as a base length. The focal length of the objective optical system for the rigid endoscope is generally very short. Therefore, the incident pupil diameter is very small, and the stereoscopic rigid endoscope according to the second embodiment may not have a sufficient base length.

According to the third embodiment, an optical path lengths of the objective optical systems to the relaying optical system are different. Therefore, if the objective optical systems have the same optical performance, the incident pupils thereof do not locate on a same plane and object distances become different, which results in the difference of magnifications between the right and left optical systems. In other words, according to the third embodiment, the objective optical systems having the same optical performance cannot be used.

SUMMARY OF THE INVENTION

The present invention is advantageous in that an improved stereoscopic rigid endoscope is provided which has a single relaying optical system in the insertion unit, and a pair of objective optical systems having the same optical performance. Further, the size of the tip of the insertion unit can be downsized with maintaining a sufficient length of a base line.

According to an aspect of the invention, there is provided an optical system for a stereoscopic rigid endoscope configured to form a pair of images of an object located at a position facing an insertion unit of the endoscope on a proximal side of the insertion unit. The endoscope is provided with a first objective optical system and a second objective optical system which are provided inside the insertion unit and are located at positions having the same distance from a tip of the insertion unit, the first objective optical system and the second objective optical system having a predetermined clearance therebetween, an optical path combining system that polarizes light passed through the first objective optical system and light passed through the second objective optical system in directions perpendicular to each other, the beam combining system parallelly shifting the optical axes of the first objective optical system and the second objective optical system by a predetermined amount so as to coincide with each other, an angle formed between a shifting direction of the first objective optical system and a shifting direction of the second objective optical system being less than 90 degrees, a relaying optical system provided inside the insertion unit and having an optical axis that is coaxial with the optical axes of the first objective optical system and the second objective optical system made coaxial by the optical path combining system, the relaying optical system relaying the image formed by each of the first objective optical system and the second objective optical system from the position in the vicinity of the distal end of the insertion unit to a position in the vicinity of the proximal end of the insertion unit, and an optical image separating system that obtains the image formed with the light passed through the first objective optical system and the image formed with light passed through the second objective optical system separately by separating the light passed through the relaying optical system into a first component that has passed through the first objective optical system and polarized by the optical path combining system and a second component that has passed through the second objective optical system and polarized by the optical path combining system from each other.

Optionally, the optical path combining system includes a first reflection surface and a second reflection surface that bend the optical axis of the first objective optical system in a cranked manner to parallelly shift the optical axis of the first objective optical system, a third reflection surface that bends the optical axis of the second objective optical system perpendicularly, an optical path combining surface that serves to shift the optical axis of the second objective optical system by the predetermined amount so that the optical axis of the second objective optical system coincides with the optical axis of the first objective optical system by polarizing the light passed through the first objective optical system and reflected by the first reflection surface and the second reflection surface and is directed to the relaying optical system in a first polarization direction, and by perpendicularly reflecting a component polarized in a second polarization direction which is perpendicular to the first polarization direction from among light passed through the second objective optical system and reflected by the third reflection surface so as to be directed to the relaying optical system.

In a particular case, the following condition is satisfied.

$0.75 < \phi_0/\phi_r < 1.1$, where, $\phi_0$ denotes a maximum effective diameter of the first and second objective optical systems and $\phi_r$ denotes a maximum effective diameter of the relaying optical system.

Optionally, the angle formed between the shifting directions of the optical axes of the first and second objective optical systems may satisfy a condition below:

$0.586 < \sin(\theta/2) < 0.675$, where $\theta$ denotes the angle.

Further optionally, the optical axes of the first and second objective optical systems before shifted by the optical path combining system may be substantially parallel with the optical axis of the relaying optical system.

Still optionally, the optical axis of the relaying optical system may be shifted with respect to the central axis of a sheath in which the first and second objective optical system, the optical path combining system and the relaying optical system are accommodated.

Further, the object image separating system may include a polarization beam splitter.

In this case, the optical system may further include a pair of imaging devices that capture the images formed with the light passed through the first objective optical system and the light passed through the second objective optical system, respectively, one of the pair of imaging devices being provided on an optical path of the light reflected by the polarization beam splitter, the other of the pair of imaging devices being provided on an optical path of the light passed through the polarization beam splitter.

Optionally, the object image separating system may include a liquid crystal shutter that selectively allows the light passed through the first objective optical system and polarized by the optical path combining system and the light passed through the second objective optical system and polarized by the optical path combining system alternately at every predetermined interval, and the endoscope may further include an imaging device that is located on an image side with respect to the liquid crystal shutter and captures the image formed with light passed through the first objective optical system and the image formed with the light passed through the second objective optical system alternately at every predetermined interval.

BRIEF DESCRIPTION OF THE ACCOMPANYING DRAWINGS

FIG. 1 schematically shows a configuration of a stereoscopic rigid endoscope according to a first embodiment of the invention;

DETAILED DESCRIPTION OF THE EMBODIMENTS

Referring to the accompanying drawings, stereoscopic rigid endoscopes according to embodiments of the invention will be described.

First Embodiment

Figure 1:
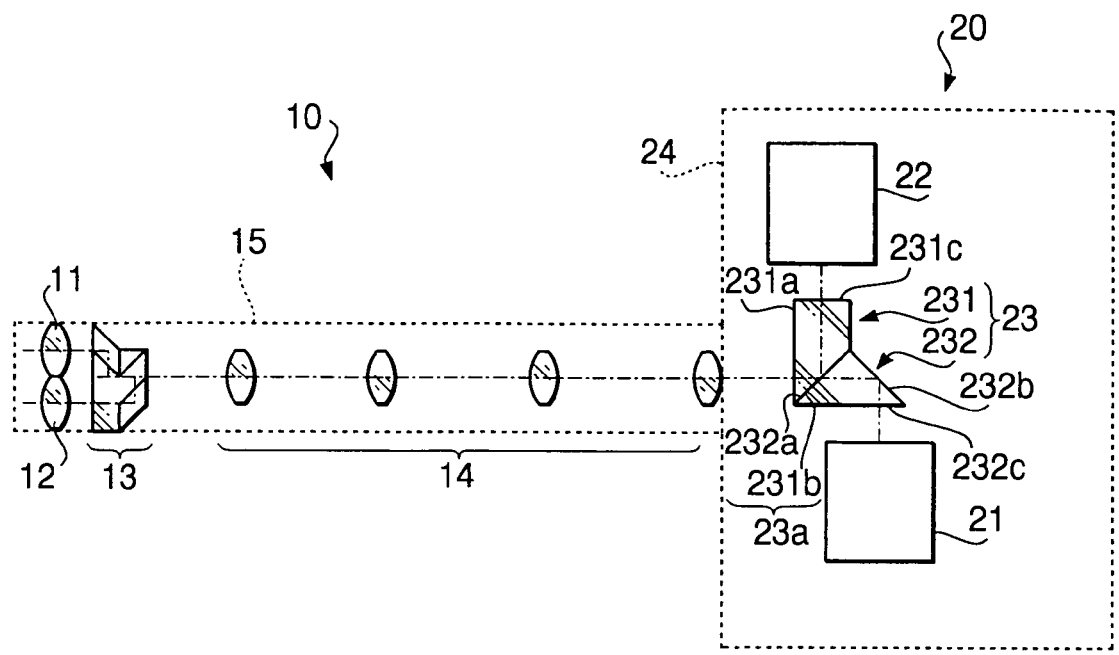

FIG. 1 schematically shows a configuration of a stereoscopic rigid endoscope according to a first embodiment of the invention. The stereoscopic rigid endoscope includes an insertion unit 10 and an image capturing unit 20.

The insertion unit 10 includes, as its principal compositions, a first objective optical system 11, a second objective optical system 12, an optical path combining element 13, a relaying optical system 14 and a sheath 15. The sheath 15 is an elongated tubular member which can be inserted inside an objective such as inside a human body, machine and fragments of broken material. The sheath 15 fixedly holds therein a lens barrel which contains the first and second objective optical systems 11 and 12 and the relaying optical system 14, and the optical path combining element 13.

The first objective optical system 11 and the second objective optical system 12 are optical systems for forming an object facing the tip of the insertion unit 10. The first and second objective optical systems 11 and 12 are arranged at positions having the same distance measured from the tip of the sheath 15. The optical axes of the objective optical systems 11 and 12 are parallel with each other, and spaced from each other by a base length, which will be described later.

The optical path combining element 13 serves to parallelly shift the optical axis of each of the first objective optical system 11 and the second objective optical system 12 by a predetermined amount so that they coincide with the optical axis of the relaying optical system 14. Therefore, an optical path length from the first objective optical system 11 to the relaying optical system 14 is equal to the optical path length from the second objective optical system 12 to the relaying optical system 14. Because of this characteristic feature, the optical systems having the same optical characteristics are used as the first and second objective optical system 11 and 12.

Further, the optical path combining element 13 converts each of the light emerging from the first objective optical system 11 and the light emerging from the second objective optical system 12 to linearly polarized light. After passed through the optical path combining element 13 and immediately before incident on the relaying optical system 14, the polarized direction of the light emerged from the first objective optical system 11 and the polarized direction of the light emerged from the second objective optical system 12 are perpendicular to each other.

The relaying optical system 14 serves to relay an image, which is formed by each of the first objective optical system 11 and the second objective optical system 12 on respective image planes, to the proximal side of the insertion unit 10. The relaying optical system 14 includes a plurality of lenses. The image formed by each of the objective optical systems 11 and 12 is, in sequence, formed on an image plane of the lenses included in the replaying optical system 14. The relaying optical system 14 is configured such that, on the most image side image plane, images having substantially the same size as those formed by the objective optical systems 11 and 12 are formed.

The image capturing unit 20 includes, as principal elements, a first imaging device 21, a second imaging device 22, an optical path splitting element 23 and a casing 24. The casing 24 is formed to have a cylindrical shape, a bottom surface of which is provided with a mechanism for allowing the proximal end of the sheath 15 of the insertion unit 10 to be detachably attached. The first and second imaging devices 2.1, 22 and the optical path splitting element 23 are secured inside the casing 24.

Each of the first and second imaging devices 21 and 22 is provided with a single-plate area image sensor having an image capturing surface provided with a two-dimensionally arranged plurality of pixels. On each image capturing surface, an on-chip color filter is provided. The imaging devices 21 and 22 convert the optical images formed on their image capturing surfaces into image data, apply various image processing, and output the processed data to a stereoscopic display such as the monitor.

The optical path splitting element 23 is an optical element that splits the light emerged from the relaying optical system 14 to the light emerged from the first objective optical system 11 and the light emerged from the second objective optical system 12. The optical path splitting element 23 has a trapezoidal prism 231 and a right angle prism 232.

Figure 2:
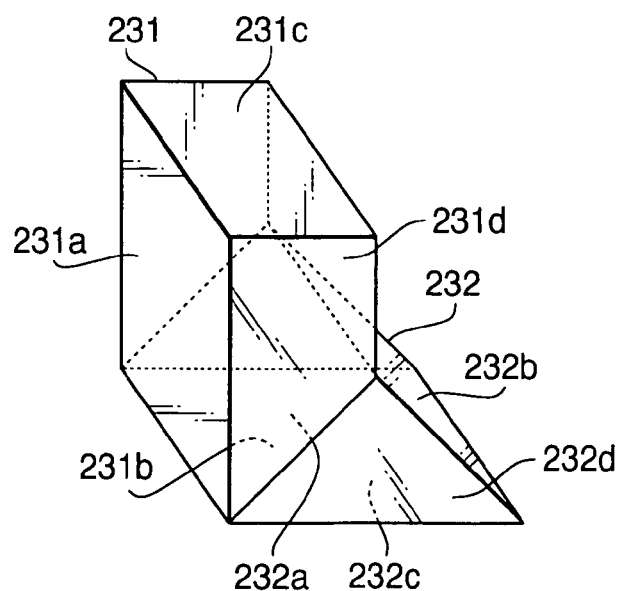
FIG. 2 is a perspective view of a trapezoidal prism and a right angle prism of an optical path splitting element.

FIG. 2 shows a perspective view of the trapezoidal prism 231 and the right angle prism 232. The trapezoidal prism 231 has a shape of a trapezoidal pole having a bottom surface 231d whose shape is a rectangular trapezoid of which a ratio of an upper base, a lower base and a height is 1:2:1. A side surface 231a connected with the lower base of the bottom surface 231d has a rectangle whose longer sides have the length same as the length of the lower base of the bottom surface 231d, and shorter sides have the length same as the length of the upper base of the bottom surface 231d. This side surface 231a will be referred to, hereinafter, as a light incident surface 231a. A side surface 231c connected with a side opposite to the inclined side of the bottom surface 231d is a square, which will be referred to as a second light emerging surface 231c hereinafter.

The right angle prism 232 has a shape of a triangular pole having a bottom surface 232d whose shape is a right-angle isosceles triangle. A side surface 232c connected with the base side of the isosceles triangle 232d has the same size as the incident surface 231a of the trapezoidal prism 231. Thus, the ratio of the shorter side to longer side of the side surface 232c is 1:2. Hereinafter, the side surface 232c will be referred to as a first light emerging surface 232c. Further, each of side surfaces 232a and 232b connected with a pair of inclined sides of the isosceles triangle has the same size as the side surface 231b of the trapezoidal prism 231. The side surface 232b will be referred to as a reflection surface 232b.

Inside the casing 24, the incident surface 231a of the trapezoidal prism 231 is perpendicular to the first light emerging surface 232c of the right angle prism 232. Further, the side surface 231b of the trapezoidal prism 231 contacts the side surface 232a. Specifically, the side surface 231b and the side surface 232a are cemented with a polarization layer, which allows the p component to pass through and reflects the s component, nipped therebetween. An optical surface constituted by a pair of side surfaces 231b and 232a and the polarization layer therebetween will be referred to as an optical path splitting surface 23a hereinafter.

When the sheath 15 is attached to the casing 24, the optical axis of the relaying optical system 14 intersects with the incident surface 231a of the trapezoidal prism 231 perpendicularly, and intersects with the optical path splitting surface 23a at 45° at the center thereof. Further, the optical path splitting element 23 is arranged such that the polarized direction of the light emerged from the first objective optical system 11 coincides with the p-polarized direction of the optical path splitting surface 23a, while the polarized direction of the light emerged from the second objective optical system 12 coincides with the s-polarized direction on the optical path splitting surface 23a. With this configuration, the light from the first objective optical system 11 passes through the optical path splitting surface 23a, and the light from the second objective optical system 12 is reflected by the optical path splitting surface 23a. That is, the optical path splitting surface 23a serves as a polarization beam splitter. Thus, the optical axis of the first objective optical system 11 penetrates the optical path splitting surface 23a, and the optical axis of the second objective optical system 12 is bent at right angle by the optical path splitting surface 23a.

After penetrating the optical path splitting surface 23a, the optical axis of the first objective optical system 11 is bent at the center of the reflection surface 232a of the right angle prism 232 in a perpendicular direction, penetrates the first light emerging surface 232c perpendicularly and reaches the image capturing surface of the first imaging device 21. As to the optical axis of the second objective optical system 12, after it is bent by the optical path splitting surface 23a in the perpendicular direction, it penetrates the center of the second light emerging surface 231c of the trapezoidal prisms 231 perpendicularly and reaches the image capturing surface of the second imaging device 22. It should be noted that the positions at which the first imaging device 21 and the second imaging device 22 are secured inside the casing 24 are adjusted so that the optical lengths from the relaying optical system 14 to respective image capturing surfaces are equal to each other.

With the above configuration, the optical path splitting element 23 functions to split the images respectively captured by the first imaging device 21 and the second imaging device 22.

Since the stereoscopic rigid endoscope according to the first embodiment has a pair of objective optical systems 11 and 12, image data of two images having parallax can be output to the monitor. Practically, however, in order to enable an observer of the images using the stereoscopic rigid endoscope to observe the images comfortably, it is preferable that a pair of images displayed on the monitor are adjusted such that the convergence point of the observer (i.e., a point where sight lines of the observer cross) coincides with an adjusting point (a focused point).

Such an adjustment can be done by inclining the optical axes of the first objective optical system 11 and the second objective optical system 12 symmetrically with respect to the optical axis of the relaying optical system 14. However, if such an adjustment method is to be taken, the diameter of the sheath should be made larger in comparison with a case where the optical axes of the objective optical systems 11 and 12, which are parallel with each other, are made close to each other. Therefore, in the stereoscopic rigid endoscope according to the first embodiment, the optical axes of the first and second objective optical systems 11 and 12 are remained substantially parallel with each other, and the convergence point is varied by shifting the central axes, which perpendicularly intersect the image capturing surfaces of the first and second imaging devices 21 and 22 at the centers thereof, respectively, with respect to the optical axes of the first and second objective optical systems 11 and 12. Alternatively, the image processing device selects a part of image data obtained by the first and second imaging devices 21 and 22 and outputs the selected part of the image data.

Next, the optical path combining element 13 will be described in detail.

Figure 3:
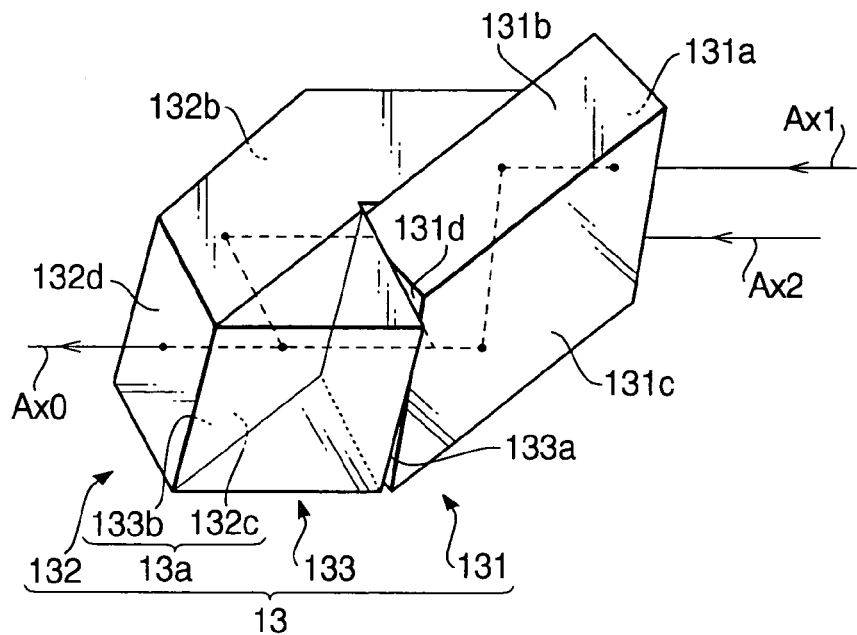
FIG. 3 is a perspective view of an optical path combining element.
Figure 4:
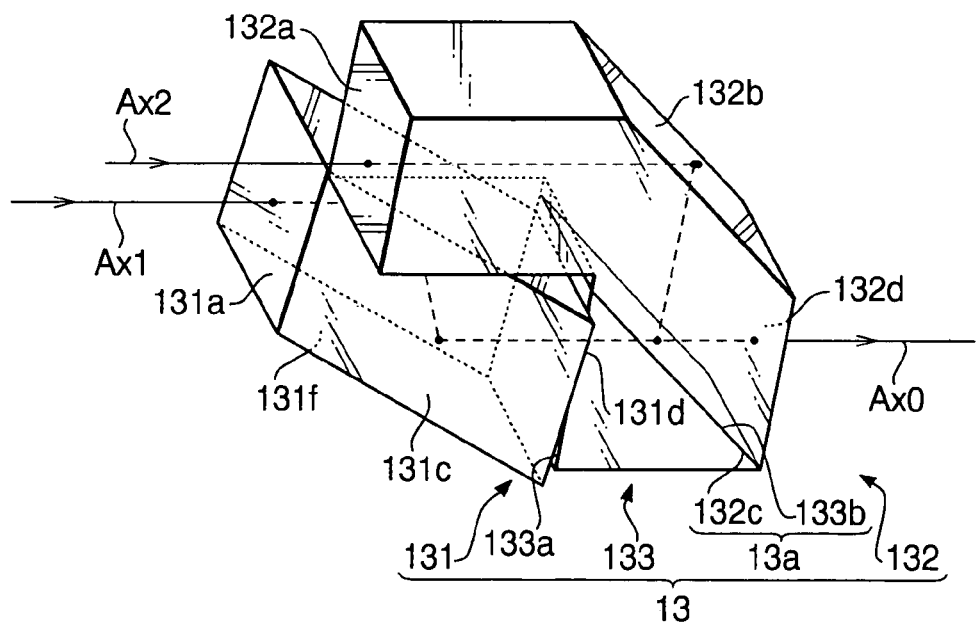
FIG. 4 is another perspective view of the optical path combining element shown in FIG. 3.

FIG. 3 is a perspective view, viewed from a lower side in FIG. 1, of the optical path combining element 13, and FIG. 4 is another perspective view of the optical path combining element 13, viewed from an upper side of FIG. 1. As shown in FIGS. 3 and 4, the optical path combining element 13 has a first prism 131, a second prism 132 and a third prism 133.

Figure 5:
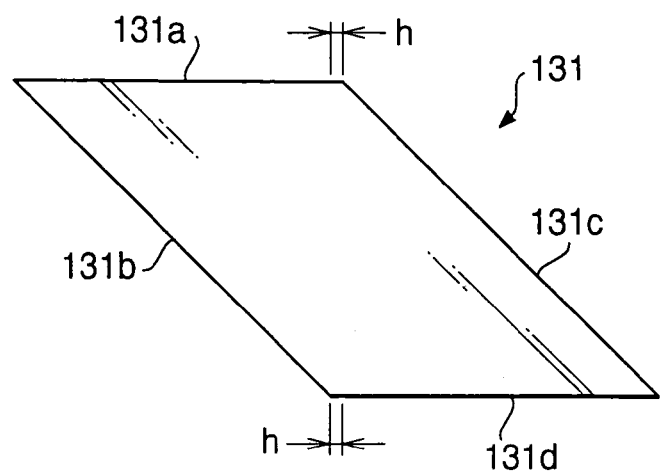
FIG. 5 is a plan view showing a shape of a bottom surface of a first prism.

The first prism 131 is a quadratic pole whose bottom surface 131f has a shape of parallelogram one inner angle is 45° and the other inner angle is 135°. FIG. 5 is a plan view showing the shape of a bottom surface 131f. Hereinafter, side surfaces 131a and 131d respectively connected with the shorter sides of the bottom surface 131f will be referred to as a first incident surface 131a and a first transmitting surface 131d. Further, side surfaces 131b and 131c respectively connected with the longer sides of the bottom surface 131f will be referred to as a first reflection surface 131b and a second reflection surface 131c.

The first prism 131 has a rectangular shape when projected on a plane parallel with the first incident surface 131a. The ratio of the longer side to the shorter side of the rectangle is approximately 1:2. The rectangle is formed such that a part of the first incident surface 131a and a part of the first transmitting surface 131d overlap by an amount having a width of h (see FIG. 5). Removing the overlapping portions when projected on the plane parallel with the first incident surface 131a, the first incident surface 131a and the first transmitting surface 131d are squares having the same size.

Figure 6:
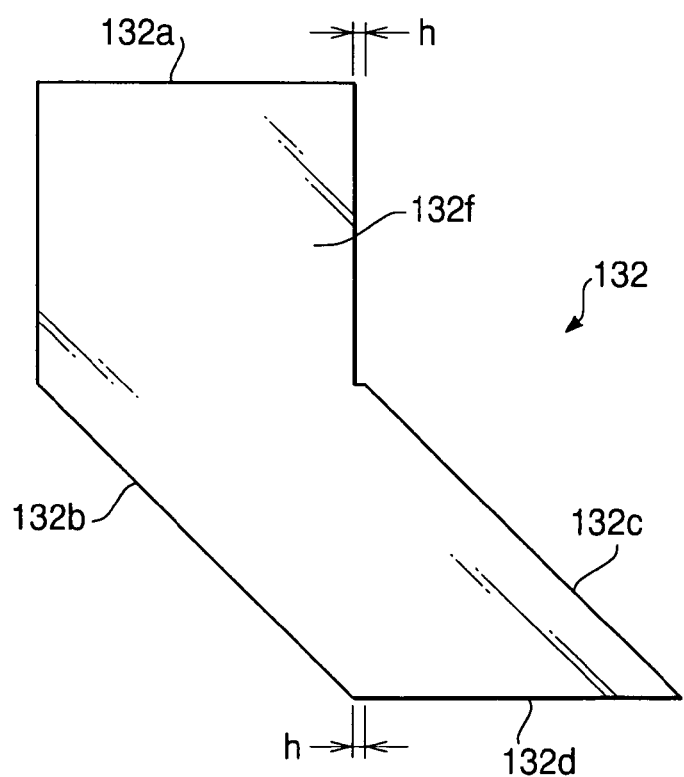
FIG. 6 is a plan view showing a shape of a bottom surface of a second prism.

The second prism 132 is a pole-like shape having a bottom surface 132f which is a particular shape. FIG. 6 is a plan view showing a shape of the bottom surface 132f of a second prism. As shown in FIG. 6, the bottom surface 132f has a shape which is equal to a combination of the above-described parallelogram (i.e., the shape of the bottom surface 131f of the first prism 131) and a square whose sides have a length equal to the length of the shorter side of the above-described parallelogram with the length h being subtracted. Further, an end of the side of the square connected with the parallelogram is aligned at a side where the inner angle at the end of the shorter side of the rectangle is smaller.

Hereinafter, a side surface 132a which is connected with a side of the bottom surface 132f opposite to a side where the parallelogram is located will be referred to as a second incident surface 132a. Further, a side surface 132d connected with a side of the bottom surface 132f opposite to a side where the square is located will be referred to as a light emerging surface. Further, the a side surface 132b which is connected with one of the longer sides of the parallelogram portion of the bottom surface 132f with an angle of 135° formed with respect to the light emerging surface 132d will be referred to as a third reflection surface 132b.

The third prism 133 is a right-angle prism. A pair of side surfaces, which have rectangular shapes, of the third prism 133 other than its inclined surface are squares having the same size of a square that is defined as the incident surface 131a of the first prism 131 with removing the above-described overlapped portion. Hereinafter, one of the side surfaces 133a will be referred to as a second transmitting surface.

The second transmitting surface 133a of the third prism 133 is parallel with the light emerging surface 132d of the second prism 132, and the inclined surface 133b of the third prism 133 contacts the side surface 132c which contacts the light emerging surface 132d of the second prism 132 with being inclined at 45°. The inclined surface 133b and the side surfaces 132c are cemented such that the four sides of each of the surfaces 133b and 132c contact each other and a polarization layer that allows the p polarization component to transmit and reflects the s polarization component is sandwiched therebetween. The optical surface including the inclined surface 133b, the side surface 132c and the polarization layer therebetween will be referred to as an optical path combining surface 13a.

The first transmitting surface 131d of the first prism 131 contacts the second transmitting surface 133a with the center of the square area being arranged coaxially with the center of the second transmitting surface 133a of the third prism 133.

With the first through third prisms 131-133 being arranged as above, inside the sheath 15, the optical axis Ax1 of the first objective optical system 11 perpendicularly penetrates the center of the square area which is defined by removing the overlapped portion from the first incident surface 131a of the first prism 131. The optical axis Ax1 is then cranked (i.e., bent perpendicularly twice) by the first reflection surface 131b and the second reflection surface 131c to penetrate the center of the square area defined in the first transmitting surface 131d. Further, the optical axis Ax1 perpendicularly penetrates the center of the second transmitting surface 133a of the third prism 133, and intersects the optical path combining surface 13a at the center thereof with inclined at an angle of 45°.

Also in the sheath 15, the optical axis Ax2 of the second objective optical system 12 perpendicularly penetrates the center of the second incident surface 132a of the second prism 132. Thus, the optical axis Ax2 of the second objective optical system 12 is bent perpendicularly by the third reflection surface 132b and intersects the optical path combining surface 13a at its center with being inclined at an angle of 45°.

The optical path combining surface 13a transmits the p polarized component on the optical path combining surface 13a of the light passed through the first objective optical system 11 and reflected by the first reflection surface 131b, while reflects the s component of the light passed through the second objective optical system 12 and reflected by the third reflection surface 132b.

With the above configuration, the optical axis Ax1 of the first objective optical system 11 penetrates the optical path combining surface 13a, and the optical axis Ax2 of the second objective optical system 12 is bent perpendicularly by the optical path combining surface 13a. Accordingly, the optical axes Ax1 and Ax2 of the first and second objective optical systems 11 and 12 are made coaxial and the combined axis perpendicularly penetrates the center of the square area defined by removing the overlapped portions from the light emerging surface 132d of the second prism 132.

Further, inside the sheath 15, the optical axis Ax0 of the relaying optical system 14 perpendicularly penetrates the center of the square area defined on the light emerging surface 132d. As a result, the optical axes Ax1 and Ax2 of the pair of objective optical systems 11 and 12 are made coaxial with the optical axis Ax0 of the relaying optical system 14. Further, a shifting amount of the optical axis Ax1 of the first objective optical system 11 provided by the first reflection surface 131b and the second reflection surface 131c of the fist prism 131 is equal to the shifting amount of the optical axis Ax2 of the second objective optical system 12 provided by the third reflection surface 132b and the optical path combining surface 13a of the second prism 132. Therefore, the optical path length of from the first objective optical system 11 to the relaying optical system 14 is made equal to the optical path length of the second objective optical system 12 to the relaying optical system 14.

It should be noted that, in the optical path combining element 13, the shifting direction of the optical axis Ax1 of the first objective optical system 11 provided by the first reflection surface 131b and the second reflection surface 131c of the first prism 131 is inclined with respect to the shifting direction of the optical axis Ax2 of the second objective optical system 12 provided by the third reflection surface 132b and the optical path combining surface 13a of the second prism 132 at right angles or several degrees less than the right angles.

Figure 7:
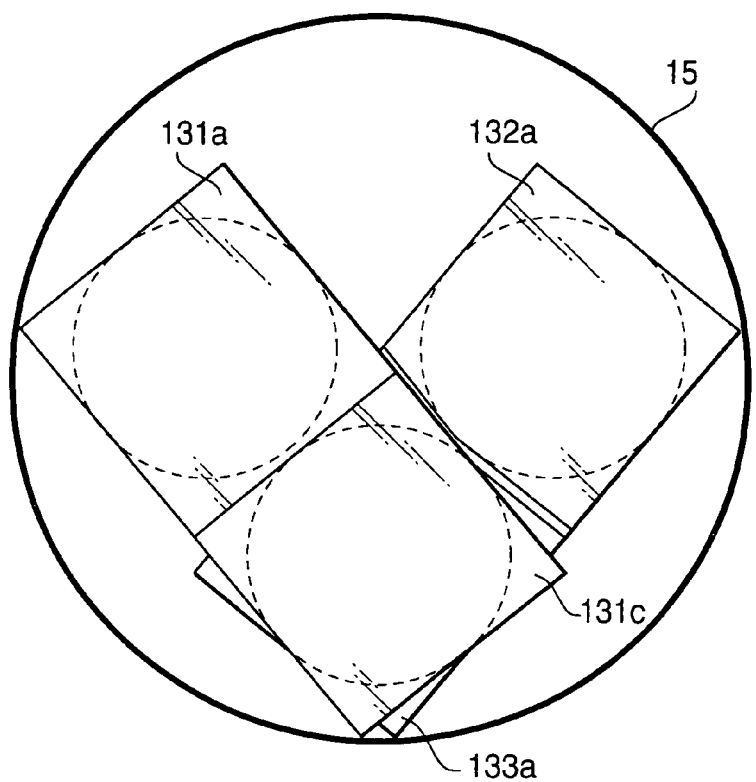
FIG. 7 is a front view of the optical path combining element viewed along optical axes of the pair of objective optical systems.

FIG. 7 is a front view of the optical path combining element 13 viewed from the first and second objective optical systems side. In FIG. 7, effective diameters of the first incident surface 131a and the second incident surface 132a are indicated by circles drawn with broken lines, and an effective diameter of the light emerging surface 132d is indicated by a circle drawn with a dotted line.

The optical path combining element 13 as described above, i.e., the optical path combining element which is configured such that the shifting directions of the optical axes Ax1 and Ax2 of the pair of objective optical systems 11 and 12 is the right angles or several degrees less than the right angles. Therefore, in comparison with a case where the shifting directions are opposite (e.g., the first embodiment of the aforementioned patent provisional publication), the optical systems 11, 12 and 14 can be arranged more densely inside the sheath 15, and it becomes possible to make the sheath more thinner.

In FIG. 7, the outer diameter of the sheath 15 is indicated by a solid line. The center of the circle indicated by the dotted line (which represents the effective diameter of the light emerging surface 132d) is shifted with respect to the center of the circle representing the sheath 15 so that the optical systems 11, 12 and 14 can be densely arranged inside the sheath 15. Since the relaying optical system 14 is fixed secured inside the sheath 15 such that the optical axis Ax0 penetrates the center of the circle drawn by the dotted line, the optical axis Ax0 of the relaying optical system 14 is shifted from the central axis of the sheath 15.

The stereoscopic rigid endoscope according to the first embodiment is configured such that the maximum effective diameter of each of the objective optical systems 11 and 12 is substantially the same as the maximum effective diameter of the relaying optical system 14. Specifically, the stereoscopic rigid endoscope according to the first embodiment is configured to satisfy condition (1) below:

$$0.75 < \phi_0/\phi_r < 1.1 \tag{1}$$

where, $\phi_0$ represents a maximum effective diameter of the first (or second) objective optical system 11 (or 12), and $\phi_r$ represents the maximum effective diameter of the relaying optical system.

If the maximum effective diameter $\phi_0$ of the objective optical system (11 or 12) is too small in comparison with the maximum effective diameter $\phi_r$ of the relaying optical system 14 and the ratio $\phi_0/\phi_r$ is smaller than the lower limit of condition (1), the focal length of the objective optical system becomes too short and the image circles of the objective optical systems 11 and 12 become small. In such a case, in order to obtain a necessary image magnification, the image should be magnified with the relaying optical system 14 or by introducing a magnification optical system. However, if the image is magnified, a combined f number increases and the resultant image is darkened.

If the maximum effective diameter $\phi_r$ is too small in comparison with the maximum effective diameter of the objective optical system 11 (12) and the ratio $\phi_0/\phi_r$ is greater than the upper limit of condition (1), the image circle the relaying optical system 14 can relay is too small. In such a case, in order to obtain a sufficient image magnification, a magnifying optical system should be provided to on the downstream side of the relaying optical system 14. If the image is magnified, however, a combined f number becomes too large and the image is darkened. Further, if the maximum effective diameter $\phi_r$ is too small, the number of relaying should be increased to obtain a sufficient length of the insertion unit 10. Such a configuration, however, requires the number of lens elements constituting the relaying optical system 14. If the number of lens elements is increased, due to reflection on each lens element, transparency of entire relaying optical system 14 may be decreased.

Figure 8:
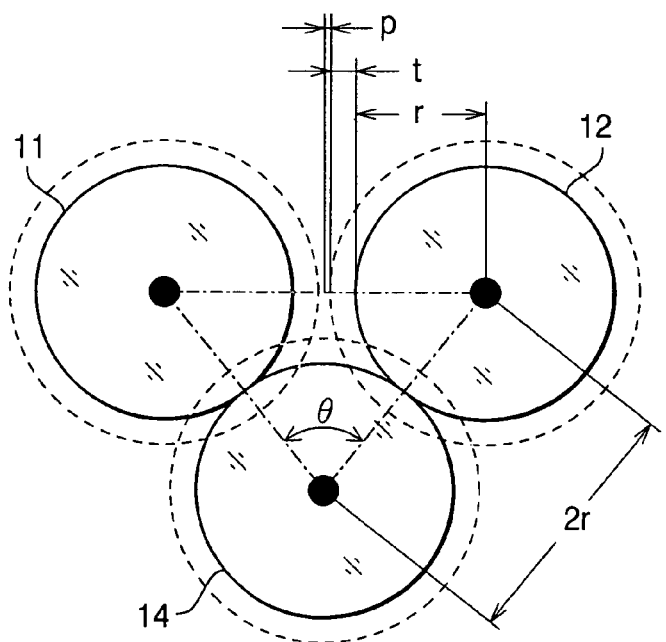
FIG. 8 is a diagram illustrating a possible angle formed between the shifting directions of the optical axes of the objective optical systems shifted by the optical path combining element.

FIG. 8 is a diagram illustrating a possible angle formed between the shifting directions of the optical axes Ax1 and Ax2 of the objective optical systems 11 and 12 shifted by the optical path combining element 13.

In FIG. 8, the circles drawn with solid lines represent effective diameter of the optical systems 11, 12 and 14 viewed along the optical axes thereof, respectively. It should be noted that the three circles drawn with solid lines have the same diameter since it is preferable, as aforementioned, that the effective diameter of the objective optical systems 11 and 12 is substantially the same as the effective diameter of the relaying optical system 14 to keep the brightness of the entire optical system. In FIG. 8, the radius of the three circles is represented by r.

In FIG. 8, another circle of broken line is drawn around each circle of solid line, each broken-line circle being coaxial with the enclosed solid-line circle. The three circles drawn with broken lines represent an outer shape of cylindrical lens barrels fixedly holding the optical systems 11, 12 and 14, respectively. The three lens barrels have the same outer size. In FIG. 8, a difference obtained by subtracting the radius r of the solid-line circle from the radius of the broken-line circle represents the thickness t of each lens barrel.

Further, each of the solid-line circle representing the first objective optical system 11 and the solid-line circle representing the second objective optical system 12 contacts the solid-line circle representing the relaying optical system 14. The above arrangement is possible because the pair of objective optical systems 11 and 12 are arranged on the opposite side of the relaying optical system 14 with the optical path combining element 13 therebetween and the lens barrels of the objective optical systems 11 and 12 do not interfere with the lens barrel of the relaying optical system 14. Further, since the lens barrel of the first objective optical system 11 should not interfere with the lens barrel of the second objective optical system 12, a clearance of 2 p is provided therebetween.

When the solid-line circles representing the optical systems 11, 12 and 14 and broken-line circles representing the outer shapes of the respective lens barrels are arranged as above, the objective optical systems 11, 12 and 14 are arranged in a most densely manner inside the sheath 15. Therefore, the angle formed by the shifting directions, by the optical path combining element 13, of the optical axes Ax1 and Ax2 of the pair of objective optical systems 11 and 12 should be made equal to a half of an angle θ which is defined as a vertex of an isosceles triangle formed by connecting the optical axes of the optical systems 11, 12 and 14. A range of the angle θ will be discussed below.

As shown in FIG. 8, a length of a pair of legs (inclined sides) forming the vertex of the isosceles triangle is 2 r, while the length of the base of the isosceles triangle is 2·(r+t+p). Therefore, the following relationship is satisfied:

$$\sin(\theta/2) = \frac{r+t+p}{2r}.$$

Further, since the length of the base of the isosceles triangle is a distance between the centers of the incident pupils of the objective optical systems 11 and 12, the length is a base length of the stereoscopic rigid endoscope.

According to the first embodiment, a half of the effective diameter (i.e., an effective radius) r of the optical system defined by the lens barrel used in the stereoscopic rigid endoscope is approximately 2 mm if the diameter of the sheath 15 is in a range of 10 mm through 12 mm, and approximately 1 mm if the diameter of the sheath 15 is in a range of 4 mm through 5 mm. Further, the thickness t of the lens barrel should be at least about 0.3 mm to provided a sufficient strength. The clearance 2p between the lens barrels of the first and second objective optical systems 11 and 12 is approximately 0.1 mm, allowing for a manufacturing error.

As a result, when the effective radius r is 2 mm, from the above relationship, $$\sin(\theta/2) = \frac{2+0.3+0.05}{2\cdot 2} = 0.5875.$$

When the effective radius is 1 mm, $$\sin(\theta/2) = \frac{1+0.3+0.05}{2\cdot 1} = 0.675.$$

Practically, the effective radius can be within a range of 1 mm through 2 mm. Accordingly, the value sin(θ/2) takes a value within a range defined by condition (2).

$$0.5675 < \sin(\theta/2) < 0.675 \tag{2}$$

By modifying condition (2), $$35.980° < \theta/2 < 42.454°,$$

and accordingly, a range of the angle θ is calculated as follows.

$$71.96° < \theta < 84.91°$$

If sin(θ/2) exceeds the upper limit of condition (2), the lens barrels respectively holding the objective optical systems II and 12 has a clearance greater than the maximum distance including the allowance of the manufacturing error. If sin(θ/2) is smaller than the lower limit of condition (2), the lens barrels of the objective optical systems 11 and 12 interfere with each other. However, such a structure is practically impossible.

Second Embodiment

Figure 9:
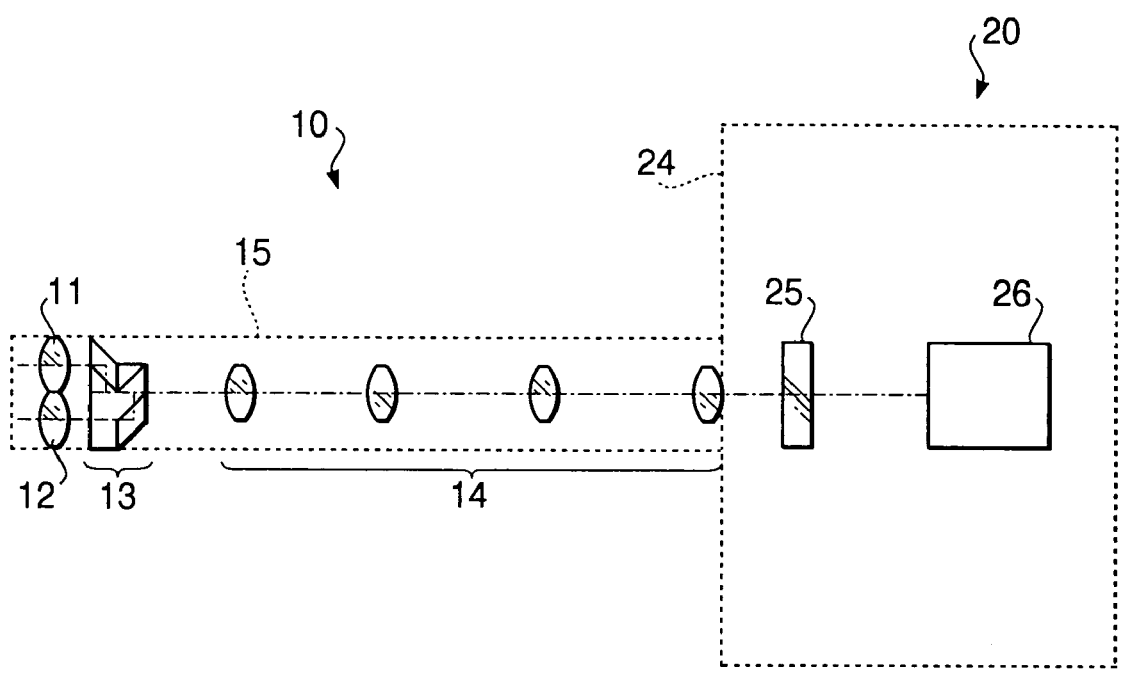
FIG. 9 schematically shows a configuration of a stereoscopic rigid endoscope according to a second embodiment of the invention.

FIG. 9 schematically shows a configuration of a stereoscopic rigid endoscope according to a second embodiment of the invention. As shown in FIG. 9, when compared with FIG. 1, the endoscope is provided with a liquid crystal (LC) shutter 25 instead of the optical path splitting element 23, and only a single imaging device 26 is provided instead of the first and second imaging devices 21 and 22 of the first embodiment. The other configuration of the second embodiment similar to that of the first embodiment, only different portions with respect to the first embodiment will be described hereinafter.

The LC shutter 25 alternately transmits a polarized light component having a predetermined polarization direction and another polarized light component having a polarization direction perpendicular to the other at a predetermined interval (e.g., one-sixtieth seconds). The LC shutter 25 is fixed inside the casing 24 of the image capturing unit 20. The LC shutter 25 is arranged such that, when the sheath 15 is coupled to the casing 24, the LC shutter 25 is on the optical axis Ax0 of the relaying optical system 14. The polarization direction of the light which the LC shutter 25 allows to transmit coincides with the polarization direction of the light passed through the first objective optical system 11. Thus, the LC shutter transmits the light passed through the first objective optical system 11 and the light passed through the second objective optical system 12 alternately at every predetermined interval.

The imaging device 26 functions in a similar manner as the first imaging device 21 and the second imaging device 22 according to the first embodiment operate. It should be noted, however, the imaging device 26 operates synchronously with the operation of the LC shutter 25 so that image data is obtained at every predetermined interval described above.

That is, the imaging device 26 obtains the image data of the image corresponding to the first objective optical system 11 and the image data of the image corresponding to the second objective optical system 12 alternately. The imaging device 26 buffers the image data of a previously obtained one of the two images using the first and second objective optical systems 11 and 12 so that a pair of images corresponding to the first and second objective optical systems 11 and 12 can be output simultaneously.

With the above configuration, the stereoscopic rigid endoscope according to the second embodiment, two image containing a parallax can be displayed on a stereoscopic displaying device such as a monitor.

The present disclosure relates to the subject matter contained in Japanese Patent Application No. 2004-007556, filed on Jan. 15, 2004, which is expressly incorporated herein by reference in its entirety.

What is claimed is:

1. An optical system for a stereoscopic rigid endoscope configured to form a pair of images of an object located at a position facing an insertion unit of the endoscope on a proximal side of the insertion unit, the endoscope comprising:

a first objective optical system and a second objective optical system which are provided inside the insertion unit and are located at positions having the same distance from a tip of the insertion unit, the first objective optical system and the second objective optical system having a predetermined clearance therebetween;

an optical path combining system that polarizes light passed through the first objective optical system and light passed through the second objective optical system in directions perpendicular to each other, the optical path combining system parallelly shifting the optical axes of the first objective optical system and the second objective optical system by a predetermined amount so as to coincide with each other, an angle formed between a shifting direction of the first objective optical system and a shifting direction of the second objective optical system being equal to or less than 90 degrees;

a relaying optical system provided inside the insertion unit and having an optical axis that is coaxial with the optical axes of the first objective optical system and the second objective optical system made coaxial by the optical path combining system, the relaying optical system relaying the image formed by each of the first objective optical system and the second objective optical system from the position in the vicinity of the distal end of the insertion unit to a position in the vicinity of the proximal end of the insertion unit; and an optical image separating system that obtains the image formed with the light passed through the first objective optical system and the image formed with light passed through the second objective optical system separately by separating the light passed through the relaying optical system into a first component that has passed through the first objective optical system and polarized by the optical path combining system and a second component that has passed through the second objective optical system and polarized by the optical path combining system from each other.

2. The optical system according to claim 1, wherein the optical path combining system includes:

a first reflection surface and a second reflection surface that bend the optical axis of the first objective optical system in a cranked manner to parallelly shift the optical axis of the first objective optical system;

a third reflection surface that bends the optical axis of the second objective optical system perpendicularly; and an optical path combining surface that serves to shift the optical axis of the second objective optical system by the predetermined amount so that the optical axis of the second objective optical system coincides with the optical axis of the first objective optical system by:

polarizing the light passed through the first objective optical system and reflected by the first reflection surface and the second reflection surface and is directed to the relaying optical system to in a first polarization direction; and perpendicularly reflecting a component polarized in a second polarization direction which is perpendicular to the first polarization direction from among light passed through the second objective optical system and reflected by the third reflection surface so as to be directed to the relaying optical system.

3. The optical system according to claim 1, wherein a condition:

$$0.75 < \phi_0/\phi_r < 1.1,$$

where, $\phi_0$ denotes a maximum effective diameter of the first and second objective optical systems and $\phi_r$ denotes a maximum effective diameter of the relaying optical system.

4. The optical system according to claim 3, wherein the angle formed between the shifting directions of the optical axes of the first and second objective optical systems satisfies a condition below:

$$0.586 < \sin(\theta/2) < 0.675,$$

where $\theta$ denotes the angle.

5. The optical system according to claim 1, wherein the optical axes of the first and second objective optical systems before shifted by the optical path combining system are substantially parallel with the optical axis of the relaying optical system.

6. The optical system according to claim 1, wherein the optical axis of the relaying optical system is shifted with respect to the central axis of a sheath in which the first and second objective optical system, the optical path combining system and the relaying optical system are accommodated.

7. The optical system according to claim 1, wherein the optical image separating system includes a polarization beam splitter.

8. The optical system according to claim 7, further comprising a pair of imaging devices that capture the images formed with the light passed through the first objective optical system and the light passed through the second objective optical system, respectively, one of the pair of imaging devices being provided on an optical path of the light reflected by the polarization beam splitter, the other of the pair of imaging devices being provided on an optical path of the light passed through the polarization beam splitter.

9. The optical system according to claim 1, wherein the optical image separating system includes a liquid crystal shutter that selectively allows the light passed through the first objective optical system and polarized by the optical path combining system and the light passed through the second objective optical system and polarized by the optical path combining system alternately at every predetermined interval; and wherein the endoscope further includes an imaging device that is located on an image side with respect to the liquid crystal shutter and captures the image formed with light passed through the first objective optical system and the image formed with the light passed through the second objective optical system alternately at every predetermined interval.

* * * * *